(12) United States Patent
Bhushan

(10) Patent No.: US 9,315,524 B2
(45) Date of Patent: Apr. 19, 2016

(54) MAGNETIC RESONANCE IMAGING AGENTS FOR CALCIFICATION

(76) Inventor: Kumar Ranjan Bhushan, St Louis, MO (US)

(*) Notice: Subject to any disclaimer, the term of this patent is extended or adjusted under 35 U.S.C. 154(b) by 1014 days.

(21) Appl. No.: 13/465,301

(22) Filed: May 7, 2012

(65) Prior Publication Data

US 2013/0296539 A1    Nov. 7, 2013

(51) Int. Cl.
*C07F 5/00*    (2006.01)

(52) U.S. Cl.
CPC ..................... *C07F 5/003* (2013.01)

(58) Field of Classification Search
CPC ........................................ C07F 5/003
See application file for complete search history.

(56) References Cited

U.S. PATENT DOCUMENTS

2002/0042539 A1* 4/2002 Arstad ............... C07B 59/004
562/21
2012/0148492 A1* 6/2012 Dozono ............. A61K 51/0489
424/1.77
2013/0123781 A1* 5/2013 Grubbs .............. A61B 17/2202
606/45
2014/0241985 A1* 8/2014 Berkman ........... A61K 51/0497
424/1.77

OTHER PUBLICATIONS

Kubicek et al., J. Am. Chem. Soc., 127(47), 2005. p. 16477-16485.*
Liu et al., Bioorganic & Medicinal Chemistry Letters, 2008, 18, p. 4789-4793.*
Bushnan et al., Angew Chem Int Ed Engl., 2007, 46(42), p. 7969-7971.*

* cited by examiner

*Primary Examiner* — Michael G Hartley
*Assistant Examiner* — Leah Schlientz

(57) ABSTRACT

The present invention discloses magnetic resonance compatible contrast agents for water-poor structures, such as bone and tissue calcification. In particular, the present invention discloses bisphosphonate-based magnetic resonance imaging contrast agents specific for hydroxyapatite, the calcium salt most commonly associated with malignant calcification.

14 Claims, 12 Drawing Sheets

MAGNETIC RESONANCE IMAGING AGENTS FOR CALCIFICATION

FIELD OF THE INVENTION

The present invention discloses magnetic resonance (MR)-compatible contrast agents for detection of water-poor structures, such as bone and tissue calcification.

BACKGROUND

Magnetic resonance imaging (MRI) has become one of the most widely used imaging modalities in clinical practice that provides soft tissue images depicting both anatomy and pathologies. Since MRI signal arises from protons, water-poor structures, such as bone and tissue calcification, are essentially invisible.

Tissue calcification is an important biomarker for human disease, with microcalcifications being of paramount importance for the detection of breast cancer. However, MRI, now the standard of care for screening high-risk women for breast cancer, is unable to detect such calcifications.

About 80% of MRI protocols in North America employ injected contrast agents that improve tissue contrast and may give additional information {Caravan, 2006; Caravan, 1999}. The most commonly used MRI contrast agents are thermodynamic and kinetically stable low molecular weight gadolinium chelates that alter the relaxivity properties of the surrounding water {Bottrill, 2006}. While a wide range of nonspecific contrast agents are being used in clinical applications for evaluation of physiological parameters, the development of efficient targeted MRI contrast agents directed at specific molecular entities has dramatically expanded the range of possible applications for MRI by combining the noninvasiveness and high spatial resolution of MRI with the specific localization of molecular targets {Weinmann, 2003}. However, previous studies aimed at the development of bone-seeking agents, have shown that the $Gd^{3+}$ complex of $DOTP^{5-}$ [1,4,7,10-Tetraazacyclododecane-1,4,7,10-tetra (methylene phosphonate)] failed to enhance the surrounding water signal when complexed to the bone {Alves, 2003}.

SUMMARY

Bisphosphonates (BPs) bind avidly to hydroxyapatite (HA) bone mineral surfaces {van Beek, 1998} and have both diagnostic {Ogawa, 2005; Lam, 2007} and therapeutic uses {Lipton, 2000}. BPs are analogues of endogenous pyrophosphates in which the hydrolysable oxygen atom that separates the two phosphate groups is replaced with a more stable carbon atom. The P-C-P structure is responsible for giving BPs their high affinity for bone, which can be further enhanced by addition of a hydroxyl group at the central carbon atom {van Beek, 1998}.

Osteoblastic bone lesions are typically diagnosed using BP-based radiotracers {Lam, 2007}. MRI of bone lesions could provide superior anatomical localization, would eliminate ionizing radiation, and could be used to guide magnetic resonance spectroscopic evaluation.

The reason for the inapplicability of MRI to bone and/or solid and semi-solid like structures is two-fold: (i) lack of free water in these structures, (ii) water that is present is partially bound, resulting in the short transverse relaxation times ($T_2$). Thus, it is prohibitively difficult to visualize bone surfaces using conventional magnetic resonance (MR) methodology. Recently, MR techniques employing various ultra short echo (UTE) signal acquisition schemes have become available {Irarrazabal, 1995; Song, 1998}. Rationale for exploiting UTE pulse sequence for MRI in present invention arises from previous work showing that TE on the order of 100 μsec is capable of providing excellent MRI of bone {Bydder, 2006}. In such "solid-like" environments, transverse relaxation times ($T_2$) are very short, averaging≈1 msec for bone and several msec for periosteum. Because of these short $T_2$s, these structures are poorly seen using conventional gradient echo (GRE) or spin-echo sequences. However, UTE sequence alone is necessary but not sufficient for detecting calcification. Gd-based contrast agents specific for the calcium salt of interest, needed to be employed in conjunction with the UTE pulse sequence.

The present invention describes a preparation and application of BP-based MRI contrast agent for UTE MRI detection of HA microcalcification, a hallmark of malignant breast cancer.

Complicating the development of BP-based MRI contrast agents, however, is the proclivity of BP's to bind lanthanides, the water-poor environment of the bone surface, and the difficulty of chemical synthesis. Unlike most contrast agents and radiotracers, which are relatively immune to their aqueous environment, Gd-based MR contrast agents are highly sensitive to water (i.e., proton) access.

One aspect of the present invention seeks to provide BP-based MRI contrast agents with different spacer length between derivatives of 1,4,7,10-tetraazacyclododecane-1,4, 7,10-tetraacetic acid (DOTA) and the BP. Because of propensity of BPs to chelate metals themselves {Alves, 2003}, the BP can be added in a pre-loading strategy after metal chelation by DOTA (FIG. 1 and FIG. 2). Pre-loading of metals on DOTA eliminates the possibility of competition from in-vivo calcium for the phosphonate which could result in the release of toxic metals, such as, gadolinium. In such an aspect, linker, $H_2N$-A-COOH is an amino acid or A is independently selected from an alkane, polyethylene glycol and polypropylene glycol. M is Y, In, Gd, Eu, or a lanthanide. In one embodiment, amino acid is natural amino acid. In some embodiment, amino acid is unnatural amino acid. In some embodiment an alkane is C1-C20 straight chain carbon unit. In some embodiments, polyethylene glycol is 6 to 20 ethylene glycol unit. In some embodiments, polypropylene glycol is 6 to 20 propylene glycol unit. In some embodiments Eu is loaded for PARACEST contrast agent. In some embodiments, Y is loaded for hyperpolarized MRI contrast agent.

In an another aspect, methyl ester protected BP can be generated before metal chelation on an organic chelating ligand (FIG. 3 and FIG. 4). Methyl ester protected BP deprotection, after metal loading on an organic chelating ligand, results in contrast agent. In such an aspect, linker, $H_2N$-A-COOH is amino acid or A is independently selected from an alkane, polyethylene glycol and polypropylene glycol. M is Y, In, Gd, Eu, or a lanthanide. In one embodiment, amino acid is natural amino acid. In some embodiment, amino acid is unnatural amino acid. In some embodiment an alkane is C1-C20 straight chain carbon unit. In some embodiments, polyethylene glycol is 6 to 20 ethylene glycol unit. In some embodiments, polypropylene glycol is 6 to 20 propylene glycol unit.

In an another aspect, BPs are conjugated to an organic chelating ligand (FIG. 5 and FIG. 6) followed by metal chelation on an organic chelating ligand, results in contrast agent. In such an aspect, linker, $H_2N$-A-COOH is an amino acid or A is independently selected from an alkane, polyethylene glycol and polypropylene glycol. M is Y, In, Gd, Eu, or a lanthanide. In one embodiment, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit.

In an another aspect, the present invention provides a contrast agent represented in general formula [1], and pharmaceutically acceptable salts, hydrates and solvents thereof:

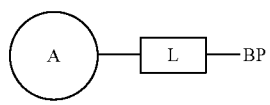

[I]

In such an aspect, BP is a bisphosphonate,

is a linker, and

is a metal chelate selected independently from:

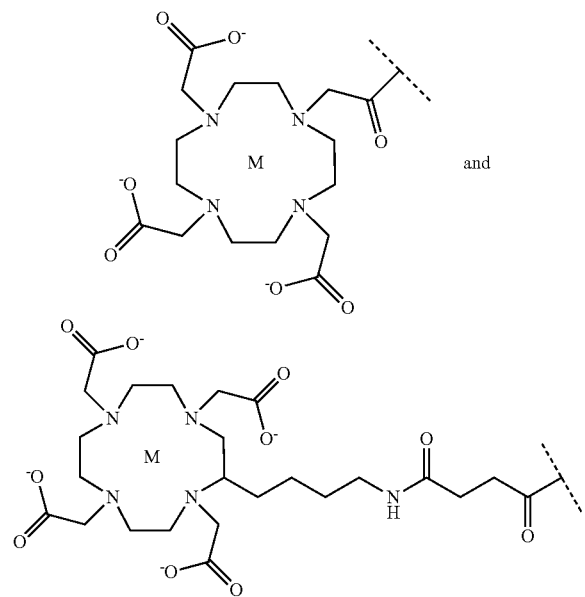

In one embodiment, bisphosphonate is independently selected from alendronate, etidronate, ibandronate, incadronate, neridronate, olpadronate, phosphonate, pamidronate, risedronate, tiludronate and zoledronate. In some embodiments, linker is independently selected from amino acid, alkane, polyethylene glycol and polypropylene glycol. In some embodiments, M is Y, In, Gd, Eu, or a lanthanide. In some embodiments Eu is loaded for PARACEST contrast agent. In some embodiments, Y is loaded for hyperpolarized MRI contrast agent. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit.

The major medical application of present invention is in the high sensitivity MRI detection of tissue calcification, especially microcalcification in breast cancer, without the need for ionizing radiation.

DETAILED DESCRIPTION

In a present invention, a synthetic strategy is developed for BP-based MRI contrast agents particularly for water-poor structure such as bone lesions and tissue calcification, and more particularly for breast cancer microcalcification. BP-based MRI contrast agents are designed in which the small molecule BPs, a targeting ligand is engineered to contain a primary amine for conjugation, and is optimized for binding affinity and physicochemical properties independent of the desired functional molecules. Functional molecules are conjugated covalently to the targeting ligands with linkers that provide adequate isolation of the two functions.

The BP-based MRI contrast agents of present invention are prepared according to the methods known in the art, as illustrated in general in FIGS. 1-6 and described for specific compounds in examples 1-6. Products are characterized by analytical HPLC, NMR and LCMS, and are obtained in typical yields of 50-60%.

Figure 1:
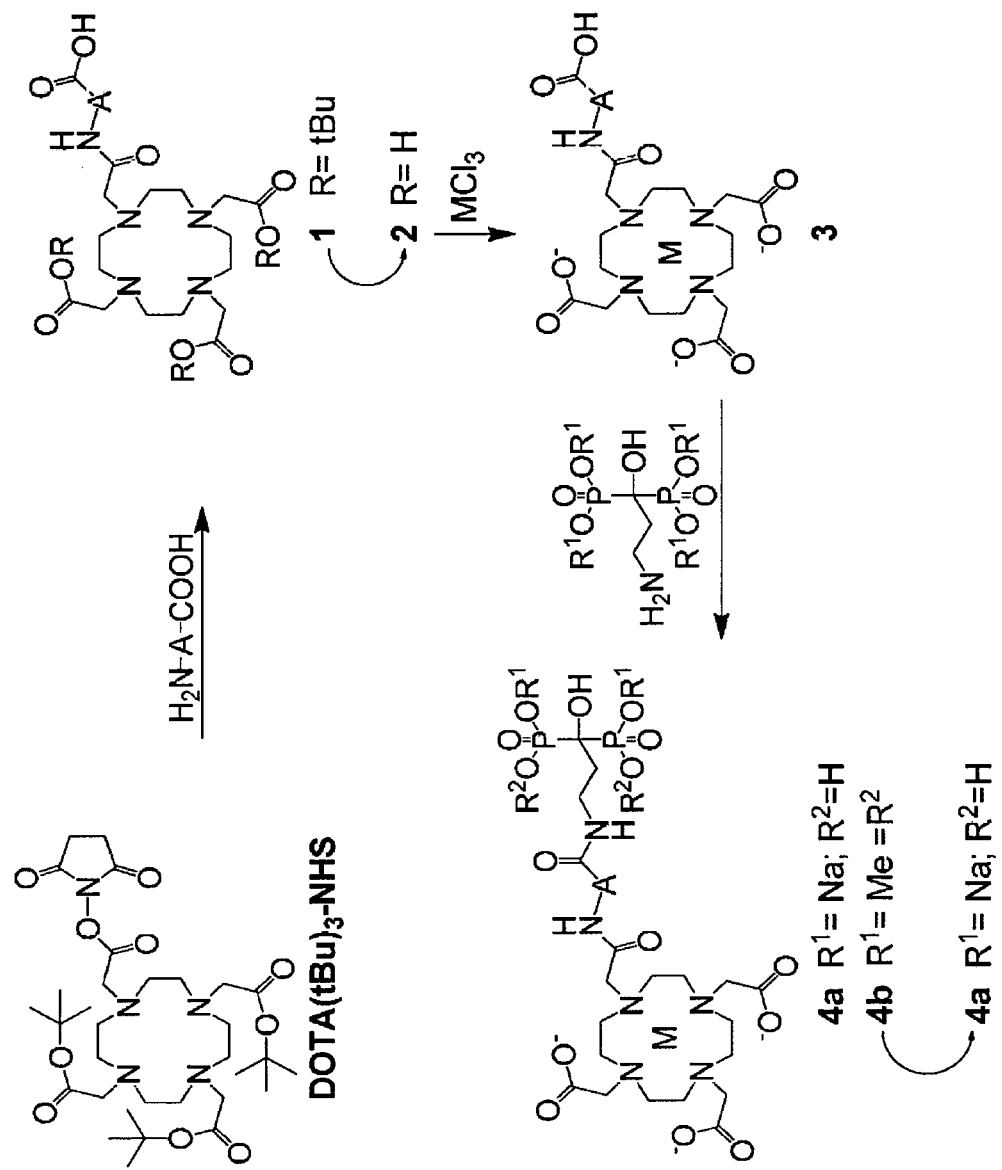
FIG. 1 represent metal hepta coordinated BP-based MRI contrast agents in which BPs can be added in a pre-loaded strategy after metal chelation by DOTA.
Figure 2:
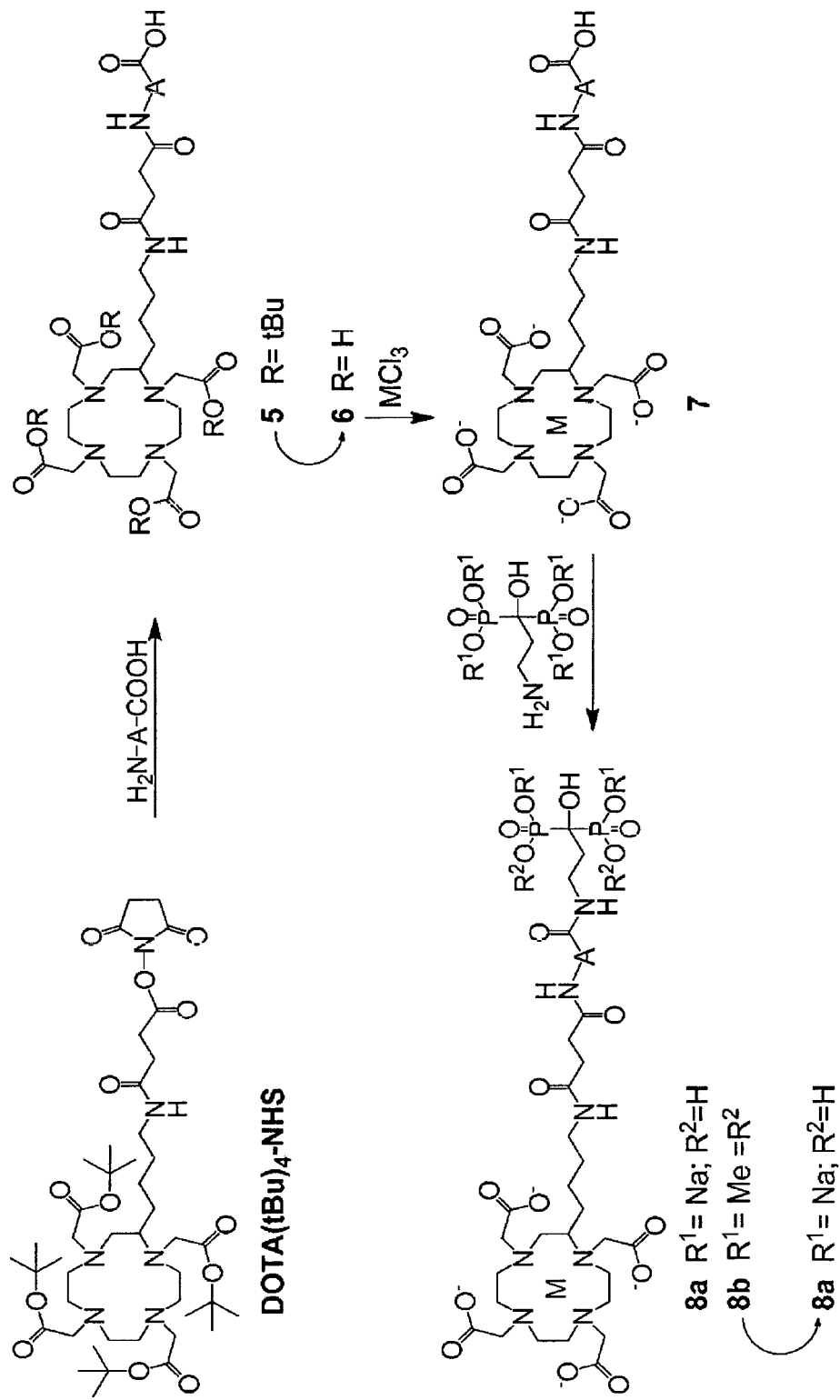
FIG. 2 represent metal octa coordinated BP-based MRI contrast agents in which BPs can be added in a pre-loaded strategy after metal chelation by DOTA.
Figure 3:
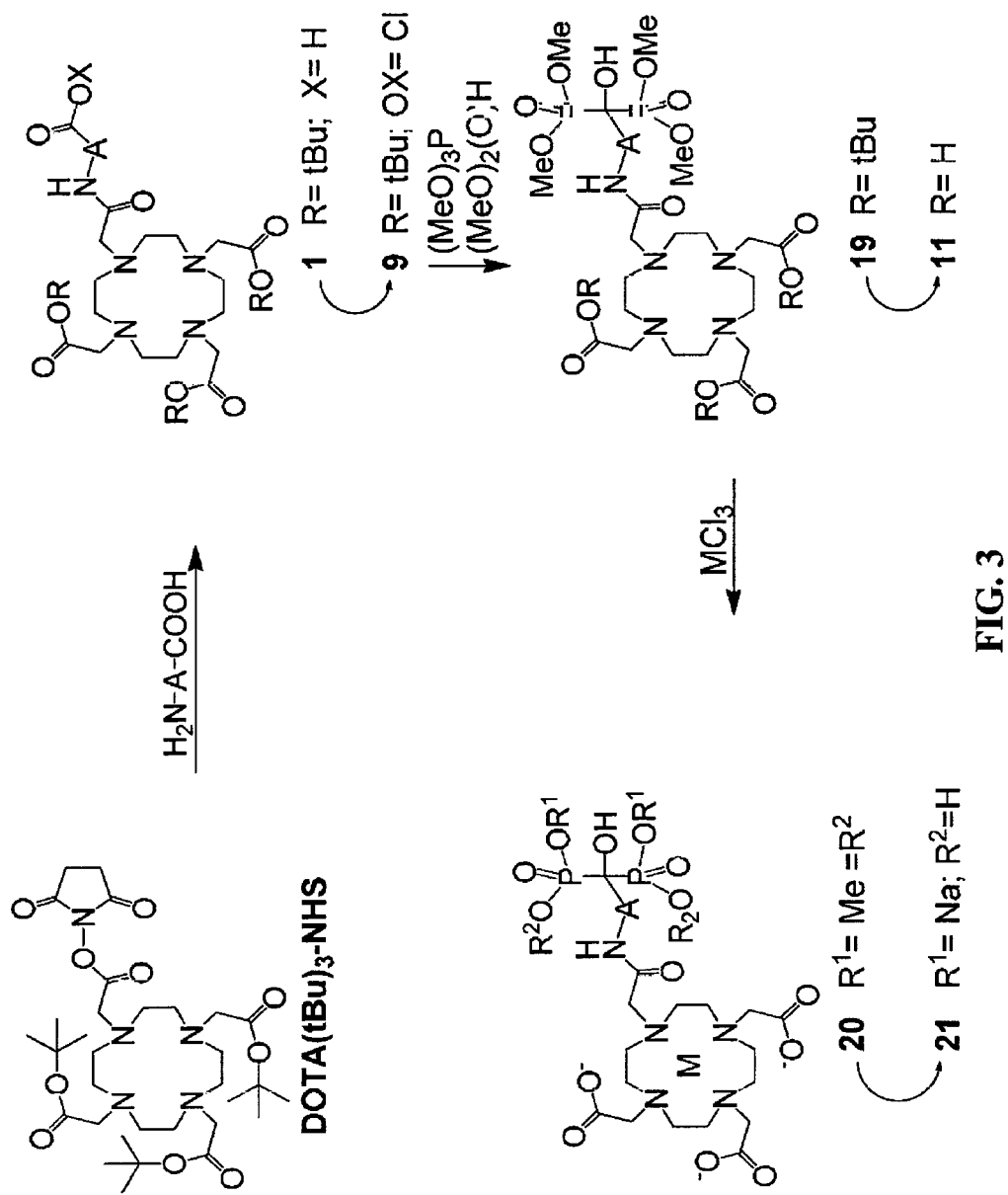
FIG. 3 represent metal hepta coordinated BP-based MRI contrast agents in which methylester protected BPs can be generated before metal chelation on an organic chelating ligand.
Figure 4:
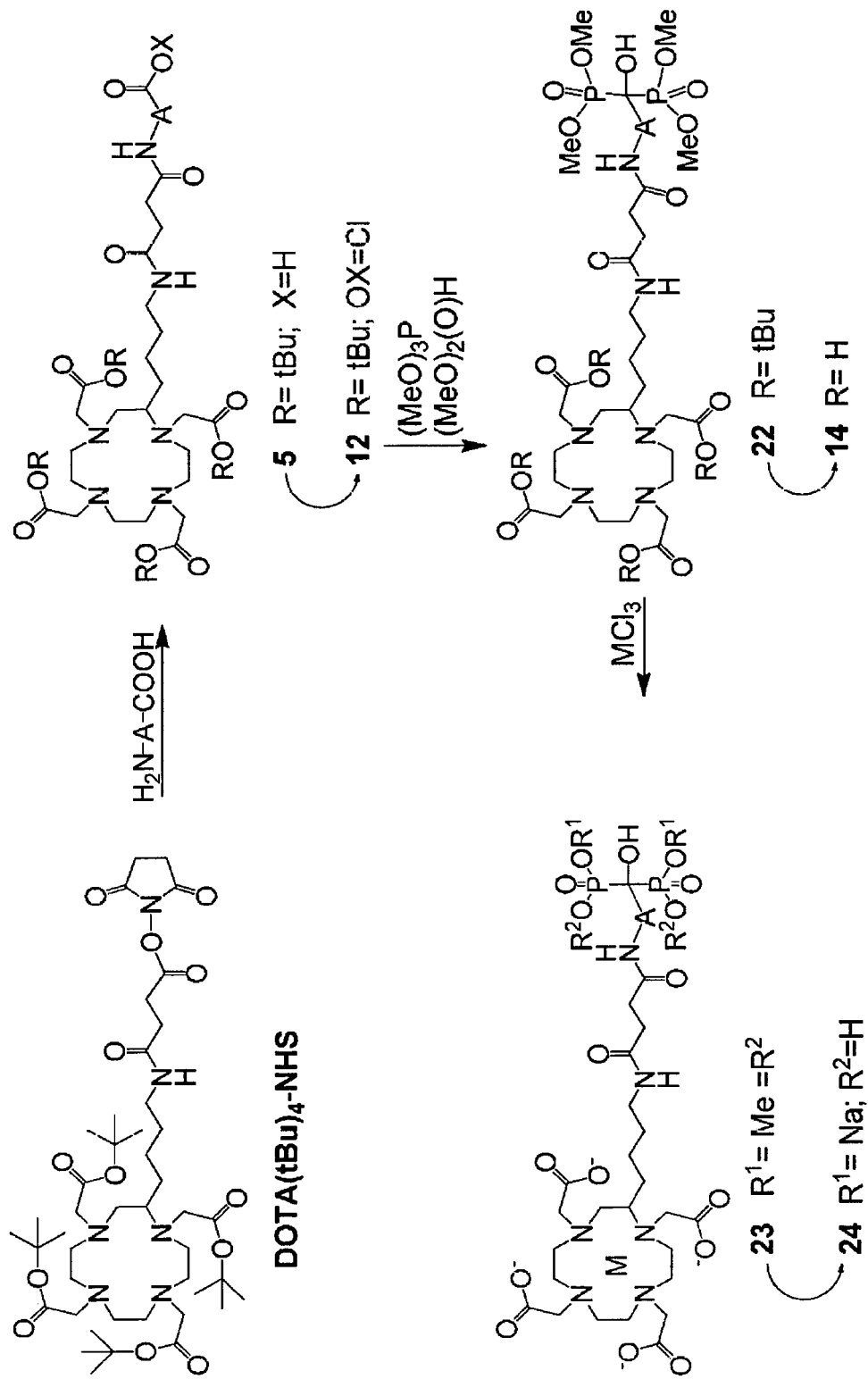
FIG. 4 represent metal octa coordinated BP-based MRI contrast agents in which methylester protected BPs can be generated before metal chelation on an organic chelating ligand.
Figure 5:
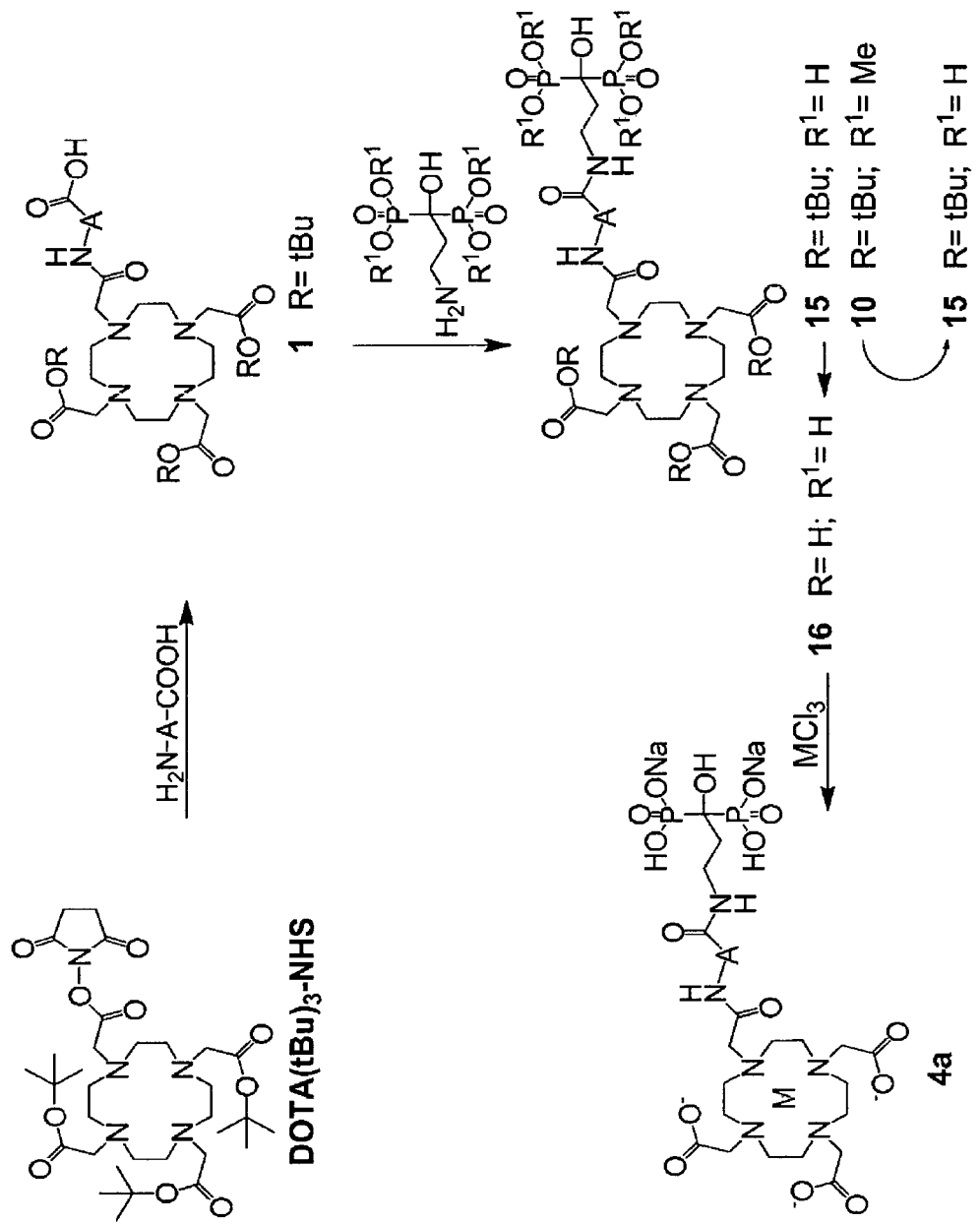
FIG. 5 represent metal hepta coordinated BP-based MRI contrast agents in which BPs are conjugated to an organic chelating ligand followed by metal loading on an organic chelating ligand.
Figure 6:
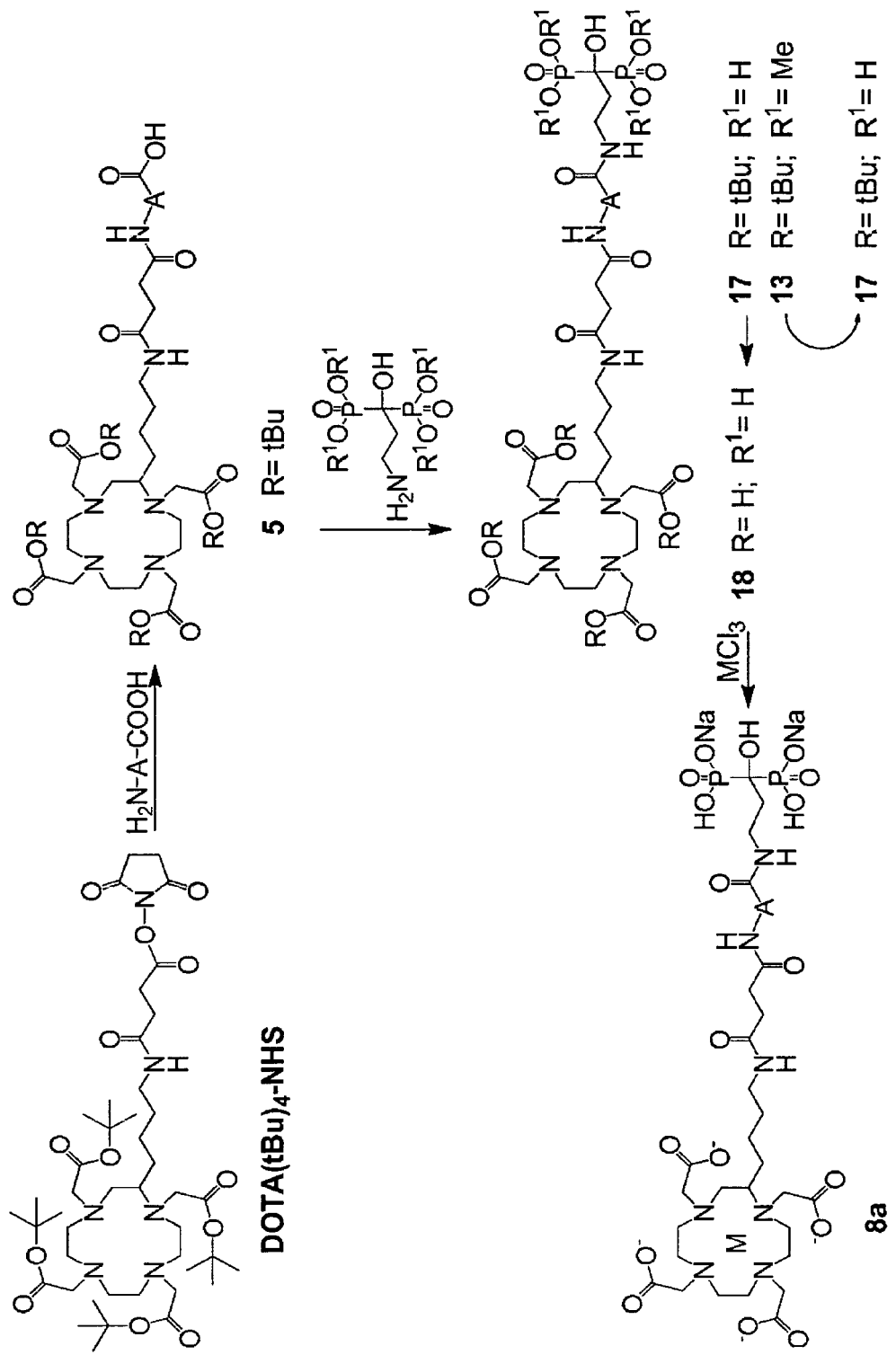
FIG. 6 represent metal octa coordinated BP-based MRI contrast agents in which BPs are conjugated to an organic chelating ligand followed by metal loading on an organic chelating ligand.

FIG. 1 of present invention describe a synthetic scheme for metal hepta coordinated BP-based MRI contrast agents in which BPs can be added in a pre-loaded strategy after metal chelation by DOTA. Linker with terminal primary amine and carboxylic acid functionality is conjugated with DOTA (tBu)$_3$-NHS and subsequent removal of protecting groups on carboxylic moiety results in intermediate for metal chelation. Metal chelation is performed by reaction with metal chloride. Carboxylic acid functional group on DOTA pre-loaded with metal is activated and conjugated with primary amine functional group of BP to results in BP-based MRI contrast agents.

In one aspect of present invention, a method for synthesizing a BP-based MRI contrast agent is provided. The method involves steps of:
(a) Starting synthesis with an organic chelating ligand selected from the group of:

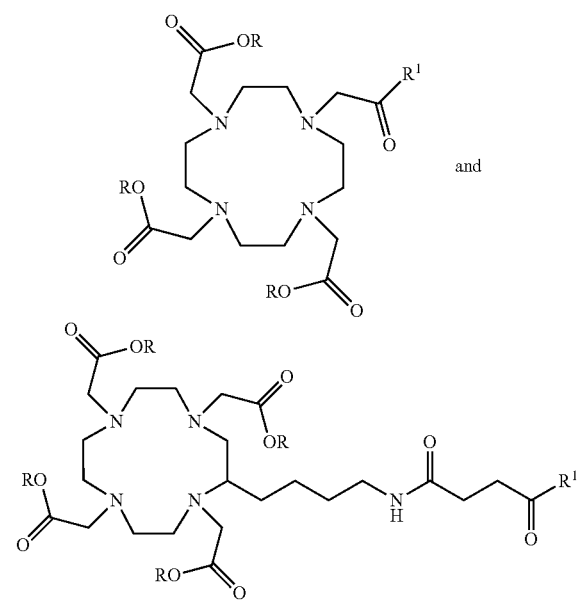

where in one embodiment R is t-butyl ester, ester or hydrogen, and
R$^1$ is

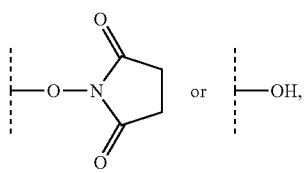

(b) reacting an organic chelating ligand with a linker having a primary amine and a carboxylic moiety at opposing ends, (c) treating the carboxylic moiety with oxalyl chloride to form an acid chloride at the carboxylic moiety, (d) reacting said acid chloride in one pot with trialkyl phosphite and dialkyl phosphite to form a alkylester protected BP, (e) deprotecting one or more carboxylic acid ester of an organic chelating ligand to yield one or more carboxylic acid functionality, (f) chelating a metal ion to result in a metal chelate, where the linker separate the metal chelate and the alkylester protected BP, and (g) deprotecting one or more BP ester of the alkylester protected BP to results in the BP-based MRI contrast agent.

In some embodiments, linker is independently selected from amino acid, alkane, polyethylene glycol and polypropylene glycol. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit. In some embodiments, alkyl is methyl, ethyl or propyl. In some embodiments, metal ion is Y, In, Gd, Eu, or a lanthanide.

In an another aspect of present invention, a method for synthesizing a BP-based MRI contrast agent is provided. The method involves steps of:
(a) Starting synthesis with an organic chelating ligand selected from the group of

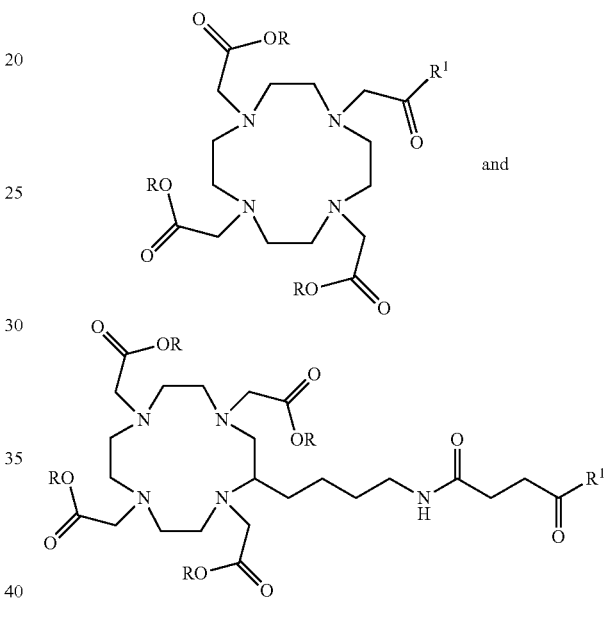

where in one embodiment R is t-butyl ester, ester or hydrogen, and
R$^1$ is

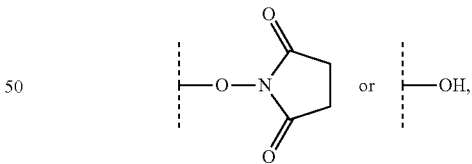

(b) reacting an organic chelating ligand with a linker having a primary amine and a carboxylic moiety at opposing ends, (c) deprotecting one or more carboxylic acid ester of the organic chelating ligand to yield one or more carboxylic acid functionality, (d) chelating a metal ion to result in a metal chelate, where a metal chelate having a carboxylic moiety, and (e) reacting an amino BP with carboxylic moiety of a metal chelate to form an amide bond to results in BP-based MRI contrast agent.

In some embodiments, linker is independently selected from amino acid, alkane, polyethylene glycol and polypropylene glycol. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit. In some embodiments, BP is independently selected from alendronate, neridronate, pamidronate, risedronate, tiludronate and zoledronate. In some embodiments, metal ion is Y, In, Gd, Flu, or a lanthanide.

In an another aspect of present invention, a method for synthesizing a BP-based MRI contrast agent is provided. The method involves steps of:
(a) Starting synthesis with an organic chelating ligand selected from the group of

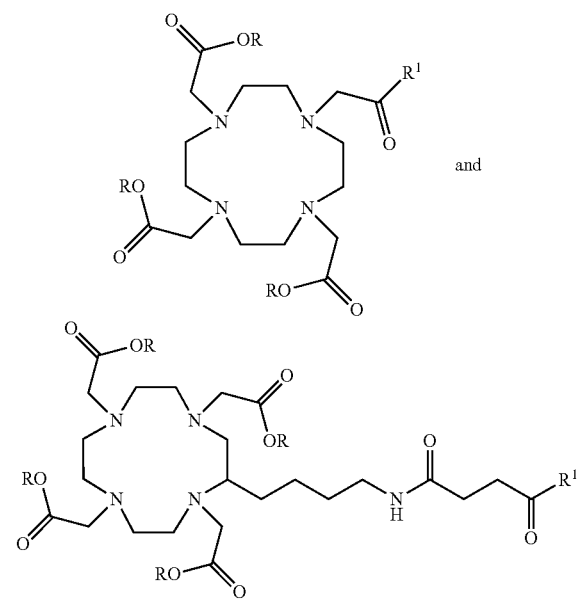

and where in one embodiment R is t-butyl ester, ester or hydrogen, and
R¹ is

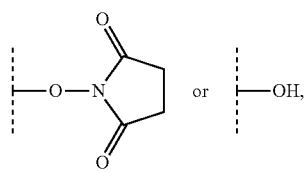

(b) reacting an amino BP with an organic chelating ligand to form an amide bond between a BP and an organic chelating ligand, (c) deprotecting one or more carboxylic acid ester of an organic chelating ligand to yield one or more carboxylic acid functionality, and (d) chelating a metal ion to one or more carboxylic acid ester of the organic chelating ligand to result in BP-based MRI contrast agent.

In some embodiments, linker separates an organic chelating ligand and the BP. In some embodiments, linker is independently selected from amino acid, alkane, polyethylene glycol and polypropylene glycol. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit. In some embodiments, BP is independently selected from alendronate, neridronate, pamidronate, risedronate, tiludronate and zoledronate. In some embodiments, metal ion is Y, In, Gd, Eu, or a lanthanide.

In an another aspect, the present invention provides a contrast agent represented in general formula [II], and pharmaceutically acceptable salts, hydrates and solvents thereof:

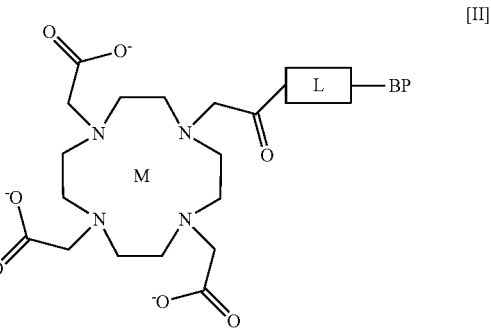

In such an aspect, BP is a bisphosphonate,

L is a linker, and
M is Y, In, Gd, Eu, or a lanthanide.

In one embodiment, bisphosphonate is independently selected from alendronate, etidronate, ibandronate, incadronate, neridronate, olpadronate, phosphonate, pamidronate, risedronate, tiludronate and zoledronate. In some embodiments, linker is independently selected from amino acid, alkane, polyethylene glycol and polypropylene glycol. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit.

In an another aspect, the present invention provides a contrast agent for MRI having a formula selected from the group of:

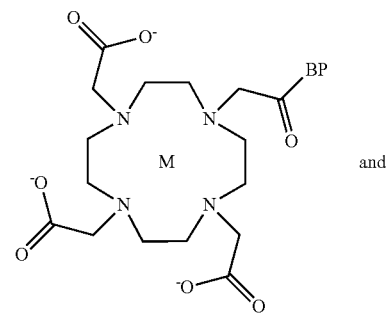

and

-continued

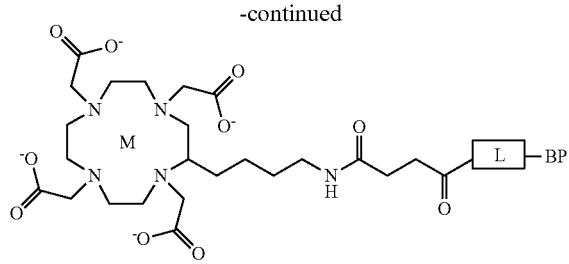

In such an aspect, BP is a bisphosphonate,

L is a linker,
and
M is Y, In, Gd, Eu, or a lanthanide.

In one embodiment, bisphosphonate is independently selected from alendronate, etidronate, ibandronate, incadronate, neridronate, olpadronate, phosphonate, pamidronate, risedronate, tiludronate and zoledronate. In some embodiments Eu is loaded for PARACEST contrast agent. In some embodiments, Y is loaded for hyperpolarized MRI contrast agent. In some embodiments, linker is independently selected from amino acid, alkane, polyethylene glycol and polypropylene glycol. In some embodiments, amino acid is natural amino acid. In some embodiments, amino acid is unnatural amino acid. In some embodiments, an alkane is C1-C20 straight chain carbon unit. In some embodiments, polyethylene glycol is 6 to 20 ethylene glycol unit. In some embodiments, polypropylene glycol is 6 to 20 propylene glycol unit.

The BP-based MRI contrast agents generated by methods of present invention can be used for many medical and non medical application that would benefit from MRI of water-poor structure such as bone lesions and tissue calcification, but none is of immediate need than breast cancer detection. In the general population, breast cancer screening employs x-ray mammography {Van Ongeval, 2006}. In 30% to 50% of cases, microcalcification is the hallmark for the presence of cancer {Morgan, 2005}, although x-ray mammography cannot distinguish the chemical form of the calcium salts present, and therefore relies on the pattern of crystal deposition {Stomper, 2003}. However, breast cancer calcifications are of two major types. Type I crystals, found more frequently in benign ductal cysts, are birefringent and colorless, and are composed of calcium oxalate {Morgan, 2005}. Type II crystals, most often seen in proliferative lesions and associated with breast cancer cells, are composed of calcium hydroxyapatite (HA), and are non-birefringent and basophilic {Haka, 2002}. Because of the relatively low sensitivity and specificity of x-ray mammography, MRI has become the standard of care for screening women at high genetic risk of the disease {Saslow, 2007}. Yet, the sensitivity and specificity of MR in this setting, estimated to be 80% and 90%, respectively {Lehman, 2007}, are still not high enough for maximal positive- and negative-predictive value.

HA microcalcifications are a hallmark of malignant breast cancer but cannot be detected by current clinical MRI. The major medical application of present invention is in the high sensitivity MRI detection of tissue calcification, especially microcalcification in breast cancer, without the need for ionizing radiation.

Present invention demonstrates an application of UTE sequences for MRI of contrast agents bound to calcifications in-vivo and in-vitro. Relaxivity properties and adsorption affinities of the complexes are tested using HA as a model of the calcification and bone surface, over other calcium salts, such as, Ca-oxalate (CO), Ca-pyrophosphate (CPP), Ca-phosphate (CP) and Ca-carbonate (CC) salts.

For in-vitro detection of HA by MRI, after a short incubation time with [$Gd^{3+}$-DOTA]-Thr-Pam-Na (Scheme 1), UTE MRI, but not conventional gradient echo (GRE) sequence MRI is able to detect HA crystals with high sensitivity. Signal enhancement is dependent on the concentration of [$Gd^{3+}$-DOTA]-Thr-Pam-Na incubated with the HA crystals, with incubation concentrations as low as 1 μM resulting in detectable signal enhancement. Signal enhancement is also dependent on relaxation time (TR), with TR≈200 msec providing the lowest background from bulk water and the highest signal enhancement of the HA crystals.

To determine the selectivity and specificity of [$Gd^{3+}$-DOTA]-Thr-Pam-Na for HA, a major mineral component of calcifications and normal bone, over other calcium salts, in the present invention an incubation of equal quantity each of Ca-hydroxyapatite (HA), Ca-pyrophosphate (CPP), Ca-phosphate (CP), Ca-oxalate (CO) and Ca-carbonate (CC) salts with [$Gd^{3+}$-DOTA]-Thr-Pam-Na in phosphate buffered saline (PBS) is performed. UTE MRI is taken before and after washing crystals, [$Gd^{3+}$-DOTA]-Thr-Pam-Na has more than three fold higher specificity for HA over other calcium salts found in the body, and permits MRI detection of HA with good sensitivity.

For in-vivo detection of subcutaneously implanted HA crystals as a model of breast cancer microcalcification, in present invention, mice with subcutaneously implanted HA slurries (in PBS) are imaged by both UTE MRI and microCT after intravenous (IV) injection of [$Gd^{3+}$-DOTA]-Thr-Pam-Na. After a minimum of 4 h of clearance, and consistent with the in-vitro results, UTE MRI provides a sensitive detection of HA crystals in-vivo, with the signal enhancement corresponding to the location of the x-ray dense crystals by microCT. Of note, the crystals are invisible by UTE MRI pre-injection of the contrast agent.

EXAMPLES

Figure 7:
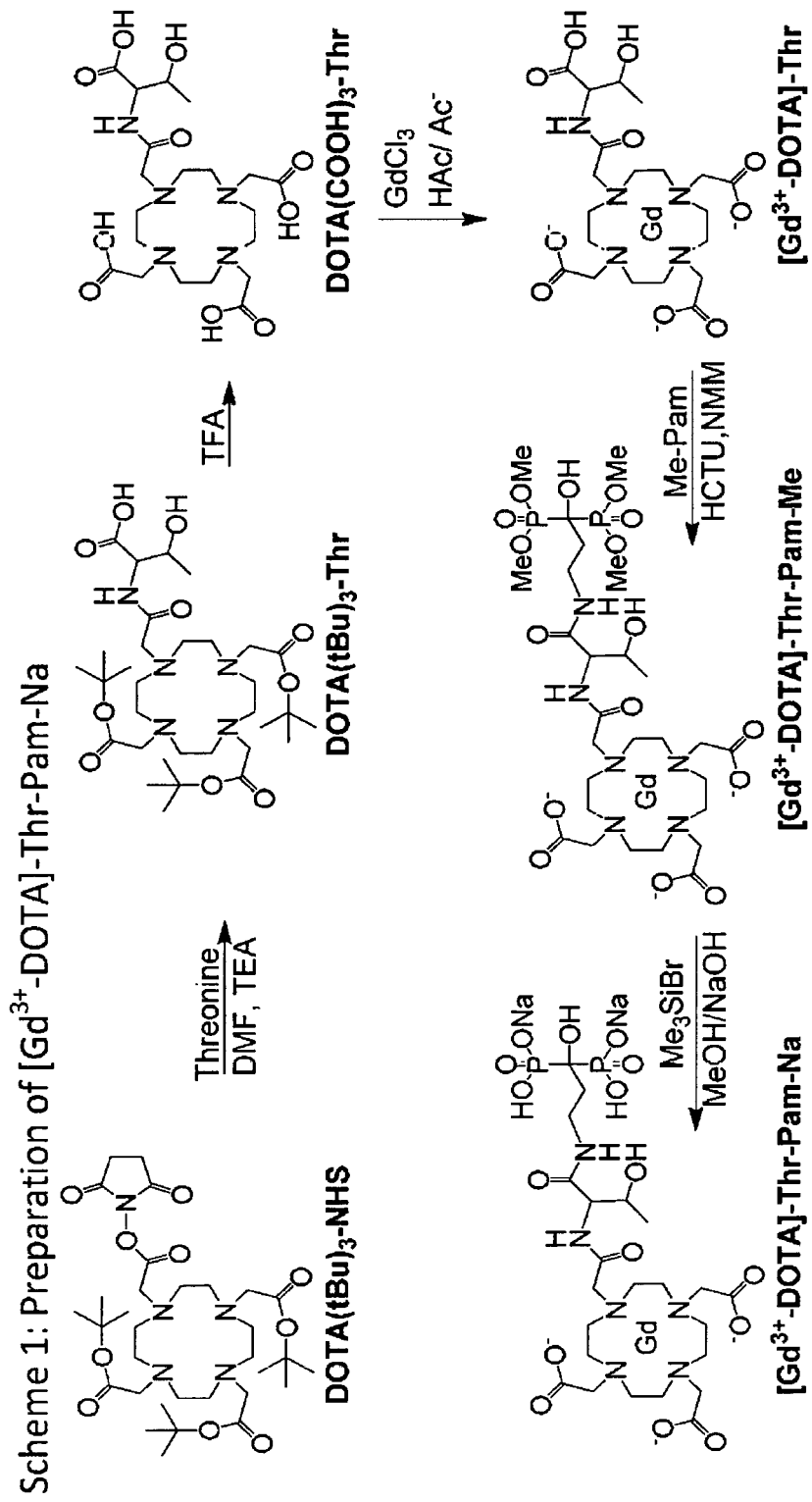
FIG. 7 is a synthetic scheme for preparation of [$Gd^{3+}$-DOTA]-Thr-Pam-Na (Scheme 1).

1. Preparation of [$Gd^{3+}$-DOTA]-Thr-Pam-Na (Scheme 1; FIG. 7)

DOTA(tBu)$_3$-Thr (Intermediate):
To a solution of threonine (0.19 mmol) in 0.1 mL water and dimethylformamide (DMF; 0.4 mL) at 0° C., is added triethylamine (TEA; 0.38 mmol) followed by dropwise addition of DOTA(tBu)$_3$-NHS ester (0.12 mmol) in dimethylformamide (DMF; 0.5 mL) for 10 min with stirring. After 10 min, the ice bath is removed and stirring continued at room temperature (RT) for 16 h. The reaction mixture is poured over 2 mL ice-cold water and purified by preparative HPLC.

DOTA(COOH)$_3$-Thr (Intermediate):
DOTA(tBu)$_3$-Thr (0.10 mmol) is taken in trifluoroacetic acid (TFA; 1 mL). The solution is stirred at RT for 2.5 h then the acid is removed by a N$_2$ stream. After lyophilization, an intermediate DOTA(COOH)$_3$-Thr is obtained without further purification as a white powder.

[$Gd^{3+}$-DOTA]-Thr (Intermediate):
The chelation of Gd is performed by adding 0.10 mL of 1 M GdCl$_3$ (0.10 mmol) in water to a solution of 0.10 mmol of DOTA(COOH)$_3$-Thr in 0.9 mL of 0.5 M acetic acid buffer (HAc/Ac⁻), pH 5.5. The reaction mixture is stirred at RT for 12 h and purification by preparative HPLC results in an intermediate [Gd$^{3+}$-DOTA]-Thr.

[Gd$^{3+}$-DOTA]-Thr-Pam-Me (Intermediate):

Me-Pam {Bhushan, 2007} (0.01 mmol), O-(6-Chlorobenzotriazol-1-yl)-N,N,N',N'-tetramethyluronium hexafluorophosphate (HCTU; 0.01 mmol), and N-methylmorpholine (NMM; 0.01 mmol) are added at RT under N$_2$ atmosphere to 0.01 mmol [Gd$^{3+}$-DOTA]-Thr in anhydrous dimethylsulfoxide (DMSO; 0.5 mL). After stirring for 1 h at RT, the reaction mixture is poured over 3 mL ice-cold water and purification by preparative HPLC results in an intermediate [Gd$^{3+}$-DOTA]-Thr-Pam-Me.

[Gd$^{3+}$-DOTA]-Thr-Pam-Na:

Trimethylsilyl bromide (Me$_3$SiBr; 0.04 mmol) is added slowly to a solution of [Gd$^{3+}$-DOTA]-Thr-Pam-Me (0.01 mmol) in dry dimethylformamide (DMF; 0.1 mL) at 0° C. under nitrogen atmosphere. The reaction mixture is vortexed at RT for 12 h. Methanolic NaOH is added to adjust pH between 4 and 4.2, vortexing for 30 min at RT followed by preparative HPLC purification results in the product [Gd$^{3+}$-DOTA]-Thr-Pam-Na.

Figure 8:
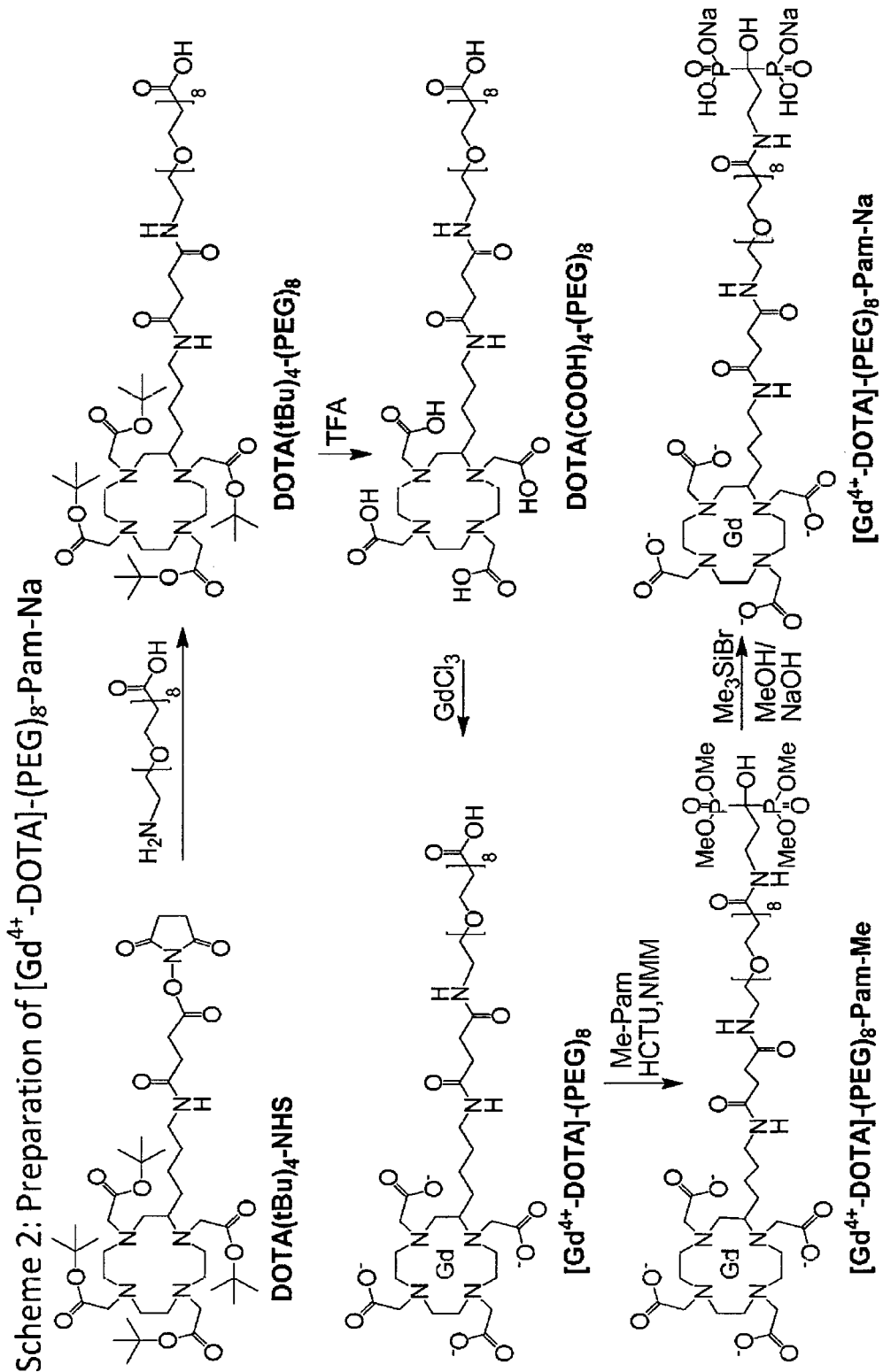
FIG. 8 is a synthetic scheme for preparation of [$Gd^{4+}$-DOTA]-(PEG)$_8$-Pam-Na (Scheme 2).

2. Preparation of [Gd$^{4+}$-DOTA]-(PEG)$_8$-Pam-Na
(Scheme 2; FIG. 8)

DOTA(tBu)$_4$-(PEG)$_8$ (Intermediate):

To a solution of Amino-(PEG)$_8$-COOH (0.19 mmol) in 0.1 mL water and dimethylformamide (DMF; 0.4 mL) at 0° C., is added triethylamine (TEA; 0.38 mmol) followed by dropwise addition of DOTA(tBu)$_4$-NHS ester (0.12 mmol) in dimethylformamide (DMF; 0.5 mL) for 10 min with stirring. After 10 min, the ice bath is removed and stirring is continued at RT for 16 h. The reaction mixture is poured over 2 mL ice-cold water and an intermediate DOTA(tBu)$_4$-(PEG)$_8$ is purified by preparative HPLC.

DOTA(COOH)$_4$-(PEG)$_8$ (Intermediate):

DOTA(tBu)$_4$-(PEG)$_8$ (0.10 mmol) is taken in trifluoroacetic acid (TFA; 1 mL). The solution is stirred at RT for 2.5 h then the acid is removed by a N$_2$ stream. After lyophilization, an intermediate DOTA(COOH)$_4$-(PEG)$_8$ is obtained without further purification as a white powder.

[Gd$^{4+}$-DOTA]-(PEG)$_8$ (Intermediate):

The chelation of Gd is performed by adding 0.15 mL of 1 M GdCl$_3$ (0.10 mmol) in water to a solution of 0.10 mmol of DOTA(COOH)$_4$-(PEG)$_8$ in 0.85 mL of 0.5 M acetic acid buffer (HAc/Ac⁻), pH 5.5. The reaction mixture is stirred at RT for 12 h and an intermediate [Gd$^{4+}$-DOTA]-(PEG)$_5$ is purified by preparative HPLC.

[Gd$^{4+}$-DOTA]-(PEG)$_8$-Pam-Me (Intermediate):

Me-Pam (0.01 mmol), O-(6-Chlorobenzotriazol-1-yl)-N,N,N',N'-tetramethyluronium hexafluorophosphate (HCTU; 0.01 mmol), and N-methylmorpholine (NMM; 0.01 mmol) are added at RT under N$_2$ atmosphere to 0.01 mmol [Gd$^{4+}$-DOTA]-(PEG)$_8$ in 1 mL anhydrous dimethylsulfoxide (DMSO; 0.5 mL). After stirring for 1 h at RT, the reaction mixture is poured over 3 mL ice-cold water and is purified by preparative HPLC to obtain an intermediate [Gd$^{4+}$-DOTA]-(PEG)$_8$-Pam-Me.

[Gd$^{4+}$-DOTA]-(PEG)$_8$-Pam-Na:

Trimethylsilyl bromide (Me$_3$SiBr; 0.04 mmol) is added slowly to a solution of [Gd$^{4+}$-DOTA]-(PEG)$_8$-Pam-Me (0.01 mmol) in dry dimethylformamide (DMF; 0.1 mL) at 0° C. under nitrogen atmosphere. The reaction mixture is vortexed at RT for 12 h. Methanolic NaOH is added to adjust pH between 4 and 4.2, being vortexed for 30 min at RT and the product [Gd$^{4+}$-DOTA]-(PEG)$_8$-Pam-Na is purified by preparative HPLC.

Figure 9:
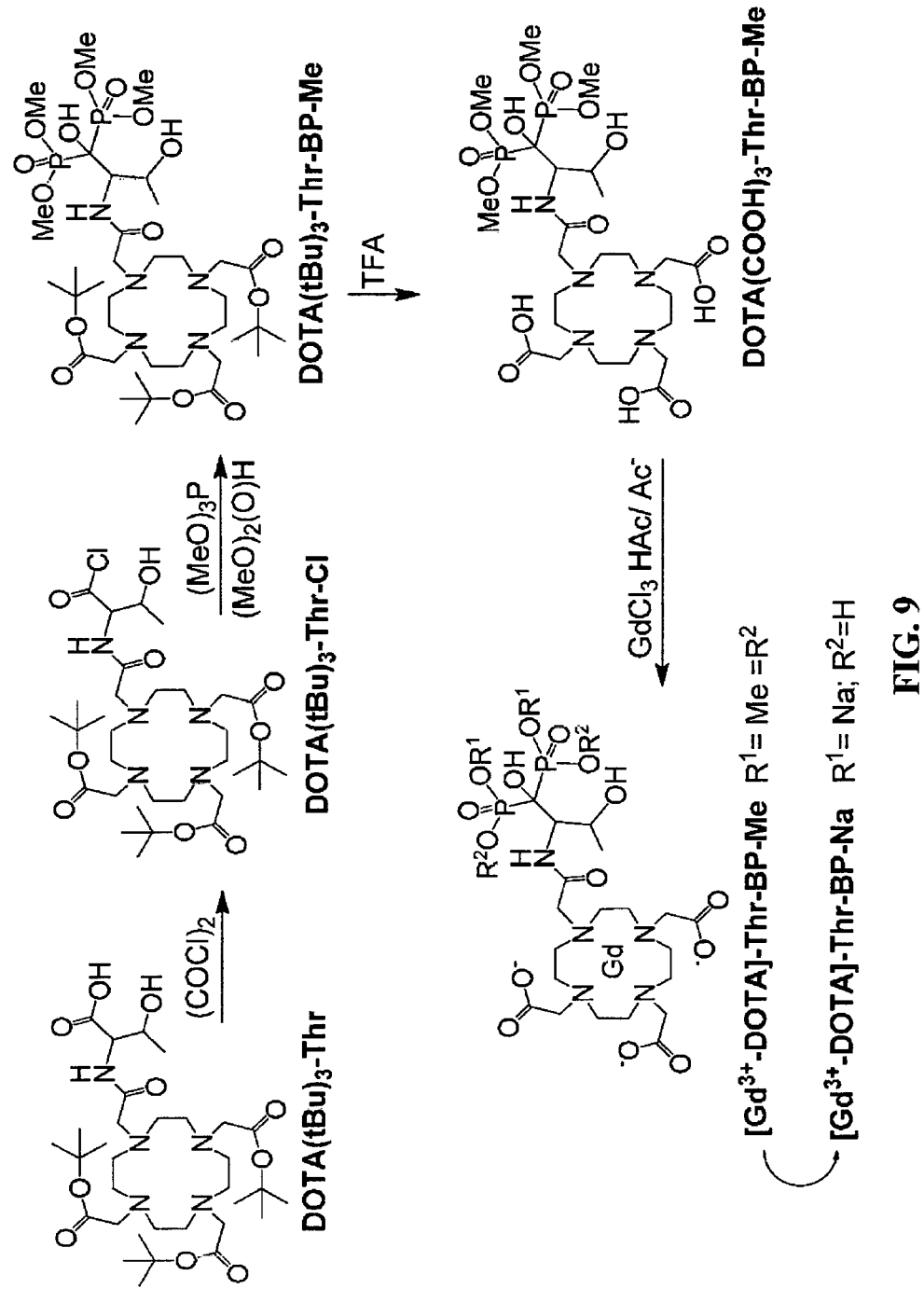
FIG. 9 is an alternative synthetic scheme for preparation of [$Gd^{3+}$-DOTA]-Thr-BP-Na (Scheme 3).

3. Preparation of [Gd$^{3+}$-DOTA]-Thr-BP-Me
(Scheme 3; FIG. 9)

DOTA(tBu)$_3$-Thr-Cl (Intermediate):

DOTA(tBu)$_3$-Thr (0.02 mmol) is taken in tetrahydrofuran (THF; 1 mL) at 0° C. under nitrogen atmosphere, is added dimethylformamide (DMF; 5 µL) and 0.04 mmol of 2 M solution of oxalyl chloride in tetrahydrofuran (THF). The solution is stirred at RT for 1 h and after that solvent is removed to get solid DOTA(tBu)$_3$-Thr-Cl which is used for next step reaction.

DOTA(tBu)$_3$-Thr-BP-Me (Intermediate):

To DOTA(tBu)$_3$-Thr-Cl (0.02 mmol), is added dropwise trimethyl phosphite (0.025 mmol) at 0° C. under nitrogen atmosphere for 5 minutes and is stirred at RT for about 30 minutes. To the above reaction mixture, is added dropwise dimethyl phosphite (0.025 mmol) at 0° C. under nitrogen atmosphere for 5 minutes and is stirred at RT for about 30 minutes then is added 2 mL cold water and an intermediate DOTA(tBu)$_3$-Thr-BP-Me is purified by preparative HPLC.

DOTA(COOH)$_3$-Thr-BP-Me (Intermediate):

DOTA(tBu)$_3$-Thr-BP-Me (0.01 mmol) is taken in trifluoroacetic acid (TFA; 1 mL). The solution is stirred at RT for 2.5 h then the acid is removed by a N$_2$ stream. After lyophilization, an intermediate DOTA(COOH)$_3$-Thr-BP-Me is obtained without further purification as a white powder.

[Gd$^{3+}$-DOTA]-Thr-BP-Me:

The chelation of Gd is performed by adding 0.10 mL of 1 M GdCl$_3$ (0.01 mmol) in water to a solution of 0.01 mmol of DOTA(COOH)$_3$-Thr-BP-Me in 0.9 mL of 0.05 M acetic acid buffer (HAc/Ac⁻), pH 5.5. The reaction mixture is stirred at RT for 12 h and product [Gd$^{3+}$-DOTA]-Thr-BP-Me is purified by preparative HPLC.

Figure 10:
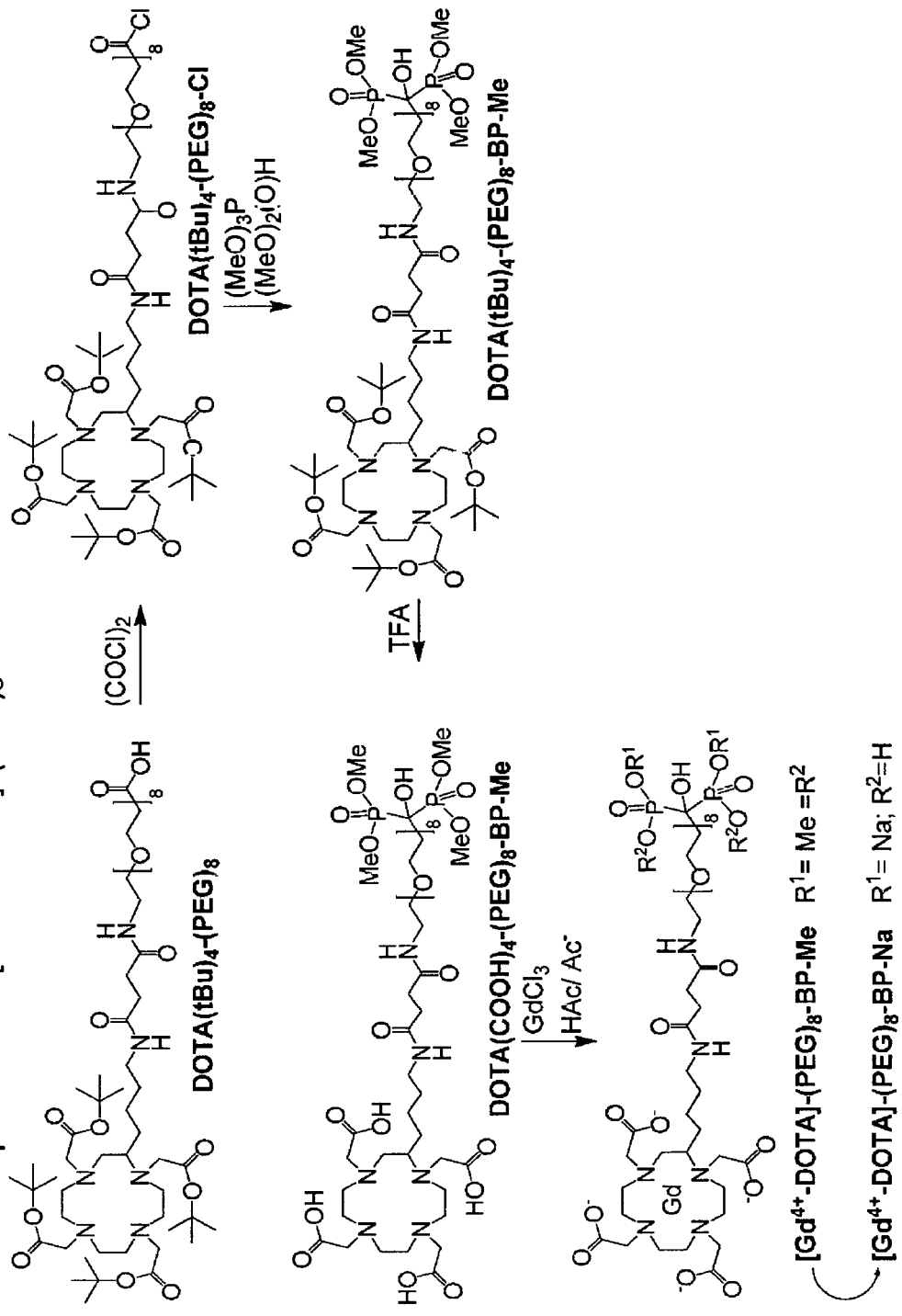
FIG. 10 is an alternative synthetic scheme for preparation of [$Gd^{4+}$-DOTA]-(PEG)$_8$-BP-Na (Scheme 4).

4. Preparation of [Gd$^{4+}$-DOTA]-(PEG)$_8$-BP-Me
(Scheme 4; FIG. 10)

DOTA(tBu)$_4$-(PEG)$_8$-Cl (Intermediate):

DOTA(tBu)$_4$-(PEG)$_8$ (0.02 mmol) is taken in tetrahydrofuran (THF; 1 mL) at 0° C. under nitrogen atmosphere, is added dimethylformamide (DMF; 5 µL) and 0.04 mmol of 2 M solution of oxalyl chloride in tetrahydrofuran (THF). The solution is stirred at RT for 1 h and after that solvent is removed to get solid DOTA(tBu)$_4$-(PEG)$_8$-Cl which is used for next step reaction.

DOTA(tBu)$_4$-(PEG)$_8$-BP-Me (Intermediate):

To DOTA(tBu)$_4$-(PEG)$_8$-Cl (0.02 mmol), is added dropwise trimethyl phosphite (0.025 mmol) at 0° C. under nitrogen atmosphere for 5 minutes and is stirred at RT for about 30 minutes. To the above reaction mixture is added dropwise dimethyl phosphite (0.025 mmol) at 0° C. under nitrogen atmosphere for 5 minutes and is stirred at RT for about 30 minutes then is added 2 mL cold water and an intermediate DOTA(tBu)$_4$-(PEG)$_8$-BP-Me is purified by preparative HPLC.

DOTA(COOH)$_4$-(PEG)$_8$-BP-Me (Intermediate):

DOTA(tBu)$_4$-(PEG)$_8$-BP-Me (0.01 mmol) is taken in trifluoroacetic acid (TFA; 1 mL). The solution is stirred at RT for 2.5 h then the acid is removed by a N$_2$ stream. After lyophilization, an intermediate DOTA(COOH)$_4$-(PEG)$_8$-BP-Me is obtained without further purification as a white powder.

[Gd$^{4+}$-DOTA]-(PEG)$_8$-BP-Me:

The chelation of Gd is performed by adding 0.15 mL of 1 M GdCl$_3$ (0.01 mmol) in water to a solution of 0.01 mmol of DOTA(COOH)$_4$-(PEG)$_8$-BP-Me in 0.85 mL of 0.05 M acetic acid butter (HAc/Ac$^-$), pH 5.5. The reaction mixture is stirred at RT for 12 h and product [Gd$^{4+}$-DOTA]-(PEG)$_8$-BP-Me is purified by preparative HPLC.

Figure 11:
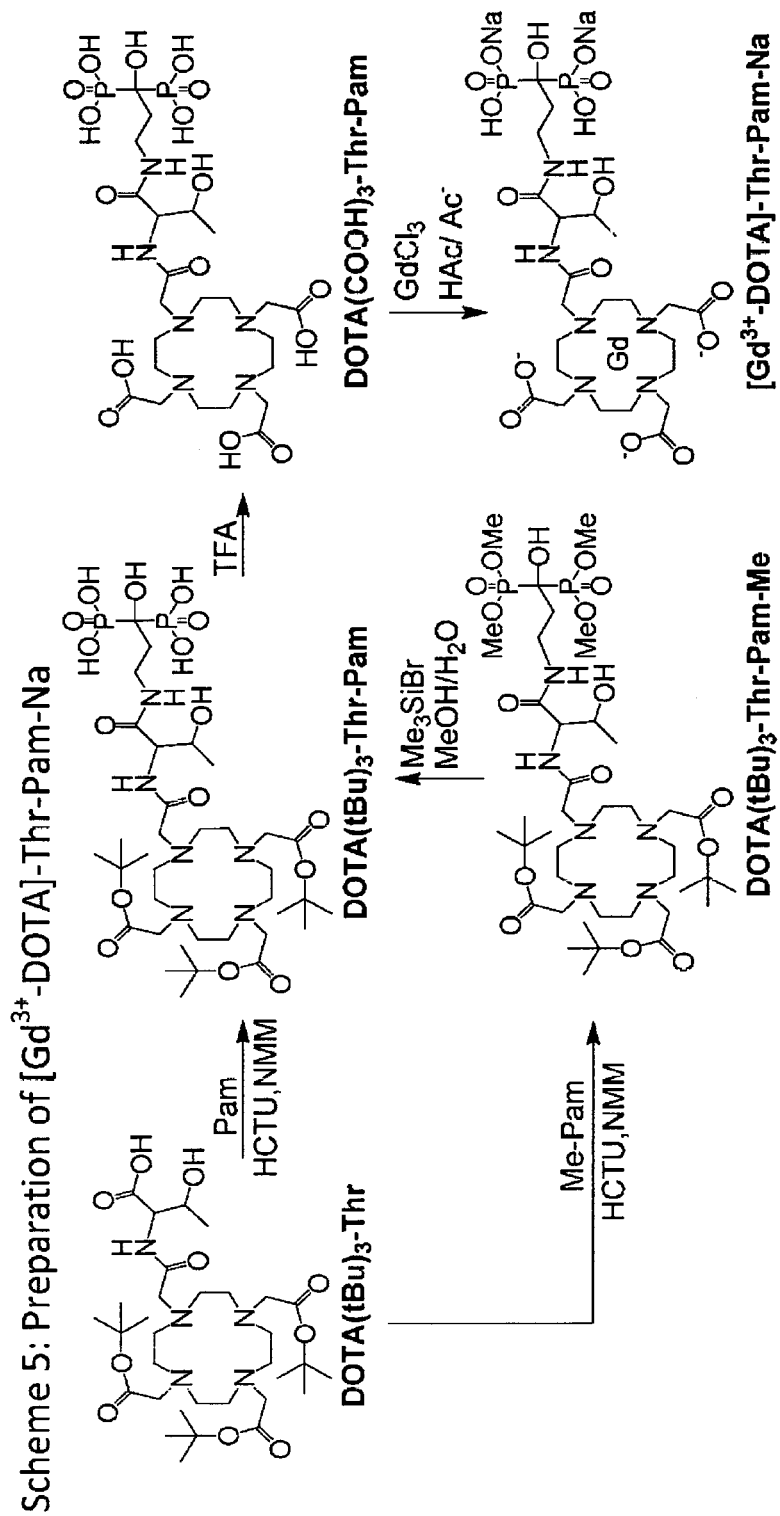
FIG. 11 is an alternative synthetic scheme for preparation of [$Gd^{3+}$-DOTA]-Thr-Pam-Na (Scheme 5).

5. Preparation of [Ge-DOTA]-Thr-Pam-Na (Scheme 5; FIG. 11)

DOTA(tBu)$_3$-Thr-Pam/DOTA(tBu)$_3$-Thr-Pam-Me (Intermediate):

Pamidronic acid/Me-Pam (0.01 mmol), O-(6-Chlorobenzotriazol-1-yl)-N,N,N',N'-tetramethyluronium hexafluorophosphate (HCTU; 0.01 mmol), and N-methylmorpholine (NMM; 0.01 mmol) are added at RT under N$_2$ atmosphere to 0.01 mmol DOTA(tBu)$_3$-Thr in anhydrous dimethylsulfoxide (DMSO; 0.5 mL). After stirring for 1 h at RT, the reaction mixture is poured over 3 mL ice-cold water and an intermediate DOTA(tBu)$_3$-Thr-Pam/DOTA(tBu)$_3$-Thr-Pam-Me is purified by preparative HPLC.

DOTA(tBu)$_3$-Thr-Pam (Intermediate):

Trimethylsilyl bromide (Me$_3$SiBr; 0.04 mmol) is added slowly to a solution of DOTA(tBu)$_3$-Thr-Pam-Me (0.01 mmol) in dry dimethylformamide (DMF; 0.1 mL) at 0° C. under nitrogen atmosphere. The reaction mixture is vortexed at RT for 12 h. Methanol/water (4/1) are added, being vortexed for 30 min at RT and an intermediate DOTA(tBu)$_3$-Thr-Pam is purified by preparative HPLC.

DOTA(COOH)$_3$-Thr-Pam (Intermediate):

DOTA(tBu)$_3$-Thr-Pam (0.01 mmol) is taken in trifluoroacetic acid (TFA; 1 mL). The solution is stirred at RT for 2.5 h then the acid is removed by a N$_2$ stream. After lyophilization, an intermediate DOTA(COOH)$_3$-Thr-Pam is obtained without further purification as a white powder.

[Gd$^{3+}$-DOTA]-Thr-Pam-Na:

The chelation of Gd is performed by adding 0.10 mL of 1 M GdCl$_3$ (0.01 mmol) in water to a solution of 0.01 mmol of DOTA(COOH)$_3$-Thr-Pam in 0.9 mL of 0.05 M acetic acid buffer (HAc/Ac$^-$), pH 5.5. The reaction mixture is stirred at RT for 12 h and product [Gd$^{3+}$-DOTA]-Thr-Pam-Na is purified by preparative HPLC.

Figure 12:
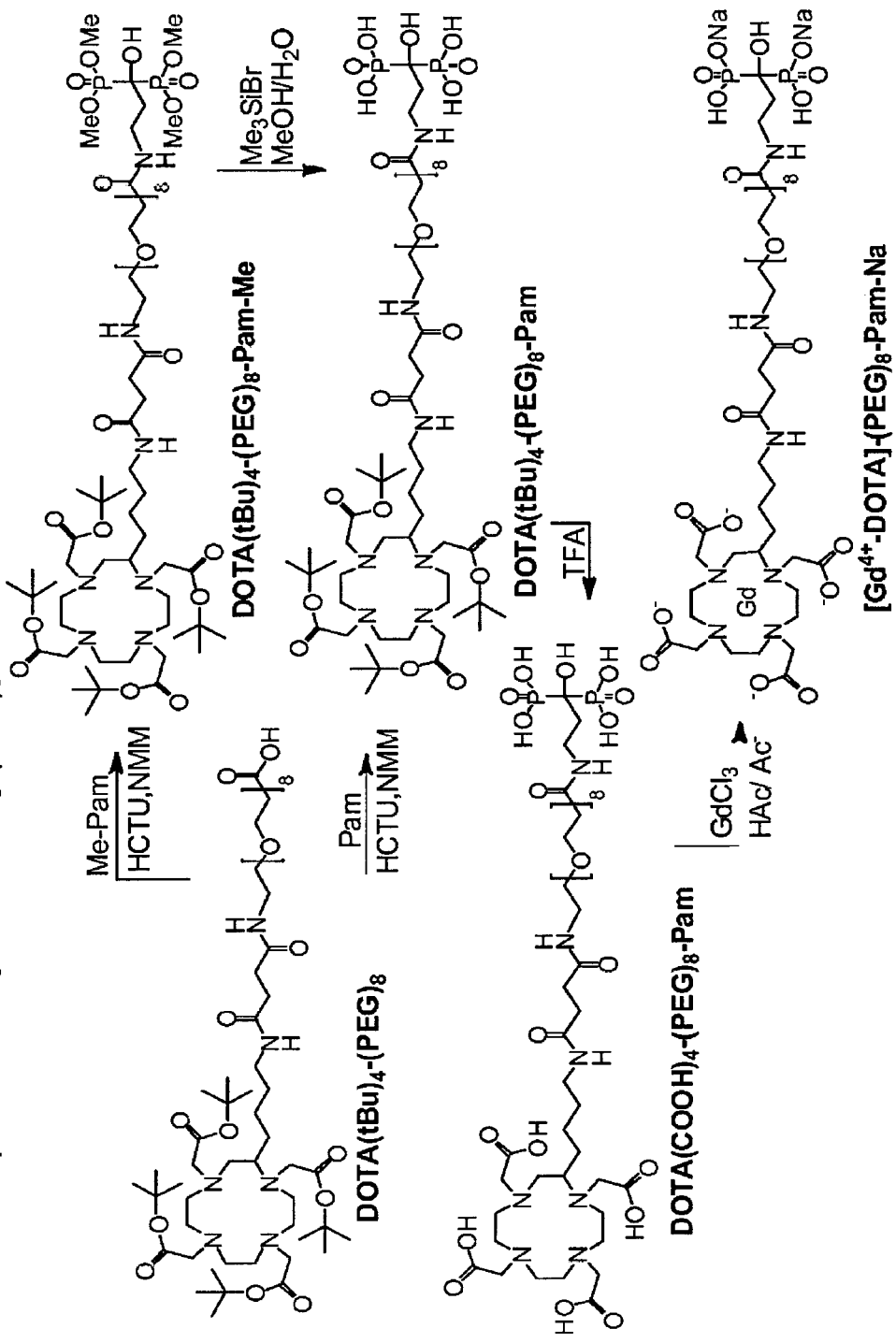
FIG. 12 is an alternative synthetic scheme for preparation of [$Gd^{4+}$-DOTA]-(PEG)$_8$-Pam-Na (Scheme 6).

6. Preparation of [Gd$^{4+}$-DOTA]-(PEG)$_8$-Pam-Na (Scheme 6; FIG. 12)

DOTA(tBu)$_4$-(PEG)$_8$-Pam/DOTA(tBu)$_4$-(PEG)$_8$-Pam-Me (Intermediate):

Pamidronic acid/Me-Pam (0.01 mmol), O-(6-Chlorobenzotriazol-1-yl)-N,N,N',N'-tetramethyluronium hexafluorophosphate (HCTU; 0.01 mmol), and N-methylmorpholine (NMM; 0.01 mmol) are added at RT under N$_2$ atmosphere to 0.01 mmol DOTA(tBu)$_4$-(PEG)$_8$ in anhydrous dimethylsulfoxide (DMSO; 0.5 mL). After stirring for 1 h at RT, the reaction mixture is poured over 3 mL ice-cold water and an intermediate DOTA(tBu)$_4$-(PEG)$_8$-Pam/DOTA(tBu)$_4$-(PEG)$_8$-Pam-Me is purified by preparative HPLC.

DOTA(tBu)$_4$-(PEG)$_8$-Pam (Intermediate):

Trimethylsilyl bromide (Me$_3$SiBr; 0.04 mmol) is added slowly to a solution of DOTA(tBu)$_4$-(PEG)$_8$-Pam-Me (0.01 mmol) in dry dimethylformamide (DMF; 0.1 mL) at 0° C. under nitrogen atmosphere. The reaction mixture is vortexed at RT for 12 h. Methanol/water (4/1) are added, being vortexed for 30 min at RT and an intermediate DOTA(tBu)$_4$-(PEG)$_8$-Pam is purified by preparative HPLC.

DOTA(COOH)$_4$-(PEG)$_8$-Pam (Intermediate):

DOTA(tBu)$_4$-(PEG)$_8$-Pam (0.01 mmol) is taken in trifluoroacetic acid (TFA; 1 mL). The solution is stirred at RT for 2.5 h then the acid removed by a N$_2$ stream. After lyophilization, an intermediate DOTA(COOH)$_4$-(PEG)$_8$-Pam is obtained without further purification as a white powder.

[Gd$^{4+}$-DOTA]-(PEG)$_8$-Pam-Na:

The chelation of Gd is performed by adding 0.15 mL of 1 M GdCl$_3$ (0.01 mmol) in water to a solution of 0.01 mmol of DOTA(COOH)$_4$-(PEG)$_8$-Pam in 0.85 mL of 0.05 M acetic acid buffer (HAc/Ac$^-$), pH 5.5. The reaction mixture is stirred at RT for 12 h and product [Gd$^{4+}$-DOTA]-(PEG)$_8$-Pam-Na is purified by preparative HPLC.

7. UTE MRI

MRI can be performed on a 1.5 T GE Signa clinical scanner equipped with a custom low-pass birdcage coil (10 cm length, 6 cm diameter). The custom UTE sequence is based on previous work in the field {Irarrazabal, 1995; Song, 1998}.

8. In-Vitro UTE and GRE MRI of HA Crystals Bound by [Gd$^{3+}$-DOTA]-Thr-Pam-Na 1 mM of [Gd$^{3+}$-DOTA]-Thr-Pam-Na is added to 5 mg of HA crystals in 50 µL PBS (pH 7.4) and is vortexed for 1 h at RT in a 1.5 mL Eppendorf tube. 5 mg HA in 1 mM of [Gd$^{3+}$-DOTA]-Thr and 50 µL PBS is used as a control. MRI, pre- and post-washing with 4×500 µL PBS, are acquired using an UTE sequence (TR=200 msec, TE=100 µsec) or conventional GRE sequence (TR=200 msec, TE=1.8 msec). Other acquisition parameters includes FOV=6 cm, slice thickness=5 mm, matrix size=256×256, NEX=4.

9. Contrast Agent Concentration and TR Dependence of UTE MRI Signals 5 mg HA is placed in 1.5 mL plastic Eppendorf tubes, then 0, 0.1, 1, 10, or 100 µM [Gd$^{3+}$-DOTA]-Thr-Pam-Na in 50 µL PBS is added to each. After vortexing 1 h at RT, the crystals are washed with 4×500 µL PBS and UTE MRI acquisition is performed using a fixed TE=100 µsec and varying TR of 17, 50, 200, 500 msec. Other acquisition parameters includes FOV=11 cm, slice thickness=10 mm, matrix size=256×256, NEX=2.

10. Quantitation of Calcium Salt Specificity 5 mg of HA or the phosphate, oxalate, carbonate, or pyrophosphate salts of calcium is placed in 1.5 ml Eppendorf tube and is incubated with 10 µM [Gd$^{3+}$-DOTA]-Thr-Pam-Na in 50 µL PBS for 1 h at RT with continuous vortexing. UTE MRI acquisition is performed pre- and post-washing with 4×500 µL PBS using TR=200 msec and TE=100 µsec. Other acquisition parameters includes FOV=9 cm, slice thickness=10 mm, matrix size=256×256, NEX=2.

11. In-Vivo Imaging of HA 50 mg of HA crystals is taken in 3004 PBS, is implanted subcutaneously at right flank of anesthetized mice. UTE MRI is taken after implantation of HA crystal using TR/TE=200 msec/100 µsec, FOV=6 cm, slice thickness=5 mm, matrix size=256×256. 4 µmol of [Gd$^{3+}$-DOTA]-Thr-Pam-Na in 300 µL saline is injected intravenously. After 4 h of clearance, an UTE MRI is taken with same parameters.

REFERENCES

1. Caravan, P. Strategies for increasing the sensitivity of gadolinium based MRI contrast agents. *Chem. Soc. Rev.* 35, 512-523 (2006).
2. Caravan, P., Ellison, J. J., McMurry, T. J. & Lauffer, R. B. Gadolinium(III) chelates as MRI contrast agents: structure, dynamics, and applications. *Chem. Rev.* 99, 2293-2352 (1999).
3. Bottrill, M., Kwok, L. & Long Nicholas, J. Lanthanides in magnetic resonance imaging. *Chem. Soc. Rev.* 35, 557-571 (2006).
4. Weinmann, H. J., Ebert, W., Misselwitz, B. & Schmitt-Willich, H. Tissue-specific MR contrast agents. *Eur. J. Radiol.* 46, 33-44 (2003).
5. Alves, F. C. et al. Silencing of phosphonate-gadolinium magnetic resonance imaging contrast by hydroxyapatite binding. *Invest. Radiol.* 38, 750-760 (2003).
6. Van Beek, E. R., Lowik, C. W., Ebetino, F. H. & Papapoulos, S. E. Binding and antiresorptive properties of heterocycle-containing bisphosphonate analogs: structure-activity relationships. *Bone* 23, 437-442 (1998).
7. Ogawa, K. et al. Development of a rhenium-186-labeled MAG3-conjugated bisphosphonate for the palliation of metastatic bone pain based on the concept of bifunctional radiopharmaceuticals. *Bioconjug. Chem.* 16, 751-757 (2005).
8. Lam, M. G. E. H., de Klerk, J. M. H., van Rijk, P. P. & Zonnenberg, B. A. Bone seeking radiopharmaceuticals for palliation of pain in cancer patients with osseous metastases. *Anti-Cancer Agents in Medicinal Chemistry* 7, 381-397 (2007).
9. Lipton, A. et al. Pamidronate prevents skeletal complications and is effective palliative treatment in women with breast carcinoma and osteolytic bone metastases: long term follow-up of two randomized, placebo-controlled trials. *Cancer* 88, 1082-1090 (2000).
10. Irarrazabal, P & Nishimura, D. G. Fast three dimensional magnetic resonance imaging. *Magn. Reson. Med.* 33, 656-662 (1995).
11. Song, H. K & Wehrli, F. W. Variable TE gradient and spin echo sequences for in vivo MR microscopy of short T2 species. *Magn. Reson. Med.* 39, 251-258 (1998).
12. Bydder, G. M. & Robson, M. D. Clinical ultrashort echo time imaging of bone and other connective tissues. *NMR Biomed.* 19, 765-780 (2006).
13. Van Ongeval, C., Bosmans, H. & Van Steen, A. Current status of digital mammography for screening and diagnosis of breast cancer. *Curr. Opin. Oncol.* 18, 547-554 (2006).
14. Morgan, M. P., Cooke, M. M. & McCarthy, G. M. Microcalcifications associated with breast cancer: an epiphenomenon or biologically significant feature of selected tumors. *J. Mammary Gland Biol. Neoplasia* 10, 181-187 (2005).
15. Stomper, P. C., Geradts, J., Edge, S. B. & Levine, E. G. Mammographic predictors of the presence and size of invasive carcinomas associated with malignant microcalcification lesions without a mass. *AJR Am. J. Roentgenol.* 181, 1679-1684 (2003).
16. Haka, A. S. et al. Identifying microcalcifications in benign and malignant breast lesions by probing differences in their chemical composition using Raman spectroscopy. *Cancer Res.* 62, 5375-5380 (2002).
17. Saslow, D. et al. American Cancer Society guidelines for breast screening with MRI as an adjunct to mammography. *CA Cancer J. Clin.* 57, 75-89 (2007).
18. Lehman, C. D. et al. Cancer yield of mammography, MR, and US in high-risk women: prospective multi-institution breast cancer screening study. *Radiology* 244, 381-388 (2007).
19. Bhushan, K. R., Tanaka, E. & Frangioni, J. V. Synthesis of conjugatable bisphosphonates for molecular imaging of large animals. *Angew. Chem. Int. Ed. Engl.* 46, 7969-7971 (2007).

What is claimed is:

1. A method of making a contrast agent, said method comprising:
   (a) providing an organic chelating ligand, wherein said organic chelating ligand selected from the group consisting of:

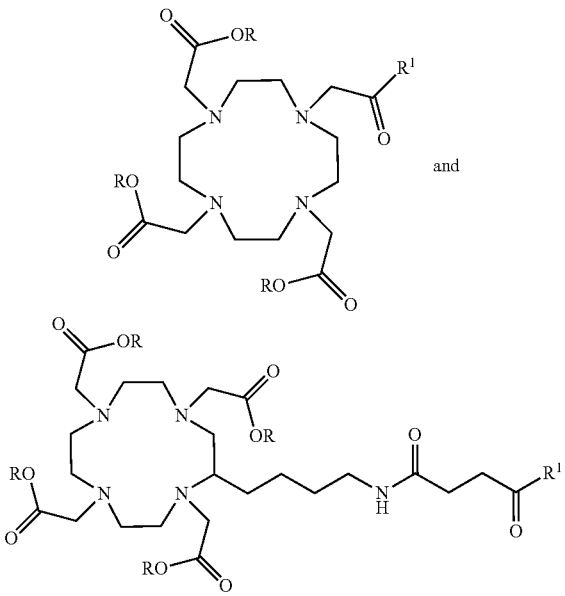

and wherein
R is t-butyl ester, ester or hydrogen;
and
$R^1$ is

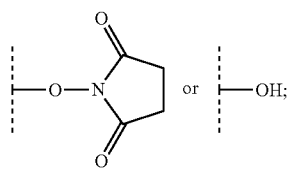

(b) reacting said organic chelating ligand with a linker, wherein said linker has a primary amine and a carboxylic moiety at opposing ends;
(c) treating said carboxylic moiety with oxalyl chloride under conditions capable of forming an acid chloride at said carboxylic moiety;
(d) reacting said acid chloride in one pot with trialkyl phosphite and dialkyl phosphite to form a alkylester protected bisphosphonate;
(e) deprotecting one or more carboxylic acid ester of said organic chelating ligand to yield one or more carboxylic acid functionality;
(f) chelating a metal ion to result in a metal chelate, wherein said linker separate said metal chelate and said alkylester protected bisphosphonate; and
(g) deprotecting one or more bisphosphonate ester of said alkylester protected bisphosphonate, wherein deprotection results in said contrast agent.

2. The method of claim 1, wherein said linker is selected from the group consisting of amino acid, alkane, polyethylene glycol and polypropylene glycol.

3. The method of claim 1, wherein said metal ion is selected from the group consisting of Y, In, Gd, Eu and lanthanide, wherein Gd is chelated for magnetic resonance imaging, Eu is chelated for CEST imaging and Y is chelated for hyperpolarized imaging.

4. The method of making the contrast agent of claim 1, wherein the contrast agent represented in general formula [I], and their pharmaceutically acceptable salts, hydrates or solvents thereof:

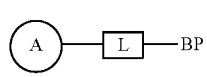

wherein
BP is a bisphosphonate;

is a linker;
and

is a metal chelate selected independently from:

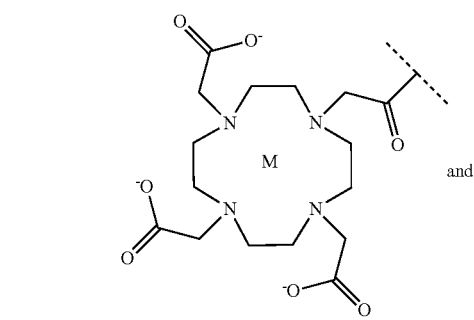

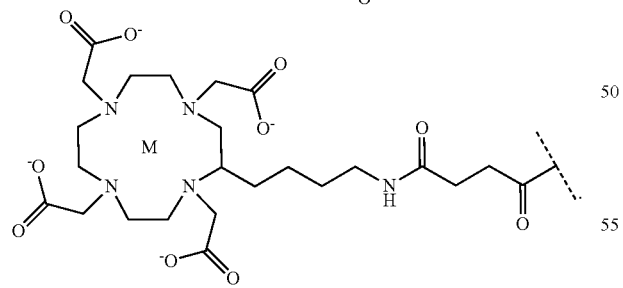

5. The method of making the contrast agent of claim 1, wherein said bisphosphonate is independently selected from the group consisting of alendronate, etidronate, ibandronate, incadronate, neridronate, olpadronate, pamidronate, risedronate, tiludronate and zoledronate.

6. The method of making the contrast agent of claim 1, wherein said linker is selected from the group consisting of amino acid, alkane, polyethylene glycol and polypropylene glycol.

7. The method of making the contrast agent of claim 1, wherein M is selected from the group consisting of Y, In, Gd, Eu and lanthanide, wherein Gd is chelated for magnetic resonance imaging, Eu is chelated for CEST imaging and Y is chelated for hyperpolarized imaging.

8. The method of making the contrast agent of claim 1, wherein the contrast agent represented in general formula [II], and their pharmaceutically acceptable salts, hydrates or solvents thereof:

[II]

wherein
BP is a bisphosphonate;

is a linker;
and
M is Y, In, Gd, Eu, or a lanthanide.

9. The method of making the contrast agent of claim 8, wherein said linker is selected from the group consisting of amino acid, alkane, polyethylene glycol and polypropylene glycol.

10. The method of making the contrast agent of claim 8, wherein said bisphosphonate is independently selected from the group consisting of alendronate, etidronate, ibandronate, incadronate, neridronate, olpadronate, pamidronate, risedronate, tiludronate and zoledronate.

11. The method of making the contrast agent of claim 1, wherein the contrast agent having a formula selected from the group consisting of:

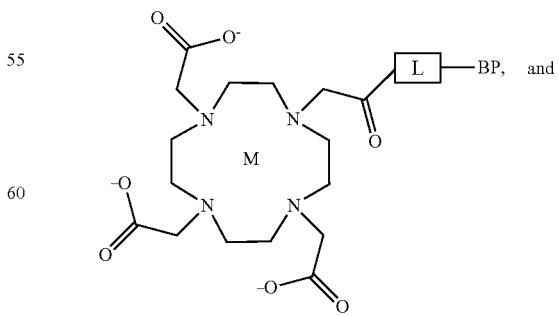

-continued

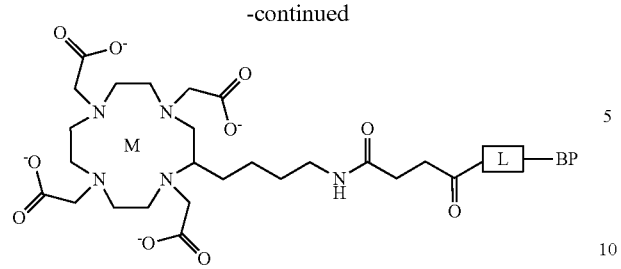

wherein
BP is a bisphosphonate;

L is a linker;
and
M is Y, In, Gd, Eu, or a lanthanide.

12. The method of making the contrast agent of claim 11, wherein said linker is selected from the group consisting of amino acid, alkane, polyethylene glycol and polypropylene glycol.

13. The method of making the contrast agent of claim 11, wherein said contrast agent is in a form of pharmaceutically acceptable salts, hydrates or solvents.

14. The method of making the contrast agent of claim 11, wherein Gd is chelated for magnetic resonance imaging, Eu is chelated for CEST imaging and Y is chelated for hyperpolarized imaging.

* * * * *